(12) United States Patent
Suzuki et al.

(10) Patent No.: US 9,778,196 B2
(45) Date of Patent: Oct. 3, 2017

(54) OPTICAL DETECTION DEVICE, OPTICAL DETECTION METHOD, AND PROGRAM

(71) Applicant: National University Corporation Tokyo University of Agriculture and Technology, Tokyo (JP)

(72) Inventors: Takayuki Suzuki, Tokyo (JP); Kazuhiko Misawa, Tokyo (JP); Yuki Obara, Tokyo (JP)

(73) Assignee: National University Corporation Tokyo University of Agriculture and Technology, Tokyo (JP)

( * ) Notice: Subject to any disclaimer, the term of this patent is extended or adjusted under 35 U.S.C. 154(b) by 0 days.

(21) Appl. No.: 15/121,373

(22) PCT Filed: Feb. 10, 2015

(86) PCT No.: PCT/JP2015/053615
§ 371 (c)(1),
(2) Date: Aug. 24, 2016

(87) PCT Pub. No.: WO2015/125665
PCT Pub. Date: Aug. 27, 2015

(65) Prior Publication Data
US 2016/0370297 A1   Dec. 22, 2016

(30) Foreign Application Priority Data
Feb. 24, 2014   (JP) .................. 2014-033129

(51) Int. Cl.
*G01J 3/44* (2006.01)
*G01N 21/65* (2006.01)

(52) U.S. Cl.
CPC ....... *G01N 21/65* (2013.01); *G01N 2021/653* (2013.01)

(58) Field of Classification Search
CPC .... G01N 21/65; G01N 2021/653; G06G 7/48; H04B 10/61; H04B 10/25; G01J 1/42; G01J 3/44; G01J 1/04; H04J 14/00
See application file for complete search history.

(56) References Cited

U.S. PATENT DOCUMENTS

2005/0280827 A1* 12/2005 Potma ................ G01J 3/44
356/485

FOREIGN PATENT DOCUMENTS

JP           2002-107301 A      4/2002

OTHER PUBLICATIONS

Takayuki, Suzuki et al., Efficient heterodyne CARS measurement by combining spectral phase modulation with temporal delay technique, Optical Express, Jun. 6, 2011, vol. 19 No. 12, pp. 11463-11470.*

(Continued)

*Primary Examiner* — Jamil Ahmed
(74) *Attorney, Agent, or Firm* — Kilpatrick Townsend & Stockton LLP

(57) ABSTRACT

A phase sensitive detection mechanism that uses electrical processing is realized, and an optical detection device, an optical detection method, and a program that are capable of detecting faint light at high speed and with high sensitivity are provided by a simple configuration.

A light source section generates a first pulsed light. A filter section transmits a second pulsed light formed from a portion of a frequency spectrum exhibited by the first pulsed light, and reflects a third pulsed light formed from another portion of the frequency spectrum exhibited by the first pulsed light. A phase modulation section phase modulates the second pulsed light at plural phases. A multiplexing section produces a fourth pulsed light by multiplexing the third pulsed light with the second pulsed light phase modu- (Continued)

lated by the phase modulation section. A detector spectrally disperses and detects scattered light generated by radiating the fourth pulsed light onto a target object. An extraction section uses specific calculation processing to synchronize with the phase modulation in the phase modulation section, so as to extract a frequency spectrum of scattered light scattered based on the second pulsed light phase modulated by the phase modulation section from the frequency spectrum of the scattered light detected by the detector.

7 Claims, 13 Drawing Sheets

(56) References Cited

OTHER PUBLICATIONS

Extended European Search Report in European Application 15752850.6 mailed Dec. 12, 2016, 4 pages.
Communication Pursuant to Article 94(3) in European Application 15752850.6 mailed Jan. 2, 2017, 6 pages.
Eesley, et al., "Optically Heterodyned Coherent Raman Spectroscopy," IEEE Journal of Quantum Electronics, vol. 14, Issue: 1, Jan. 1978, pp. 45-49.
Jurna, et al., "Background Free CARS Imaging by Phase Sensitive Heterodyne CARS," Optics Express, vol. 16, No. 20, Spetember 29, 2008, pp. 15863-15869.
Cheng, et al., "An Epi-Detected Coherent Anti-Stokes Raman Scattering (E-CARS) Microscope with High Spectral Resolution and High Sensitivity," *The Journal of Physical Chemistry B*, vol. 105, No. 7, pp. 1277-1280.
Kano, et al., "Near-infrared coherent antiStokes Raman Scattering microscopy using supercontinuum generated from a photonic crystal fiber," *Applied Physics B*, vol. 80, pp. 243-246 (2005).
Suzuki, et al., "Efficient heterodyne CARS measurement by combining spectral phase modulation with temporal delay technique," *Optics Express*, vol. 19, No. 12, pp. 11463-11470 (2011).
Suzuki, et al., "Phase-sensitive CARS spectroscopy by phase modulation of monochromatic component in broadband pulses", *IEICE Technical Report. LQE, Lasers and Quantam Electronics*, vol. 112, No. 62, pp. 1-5.
International Search Report for International Application No. PCT/JP2015/053615 mailed May 19, 2015 with English translation.

\* cited by examiner

FIG.3
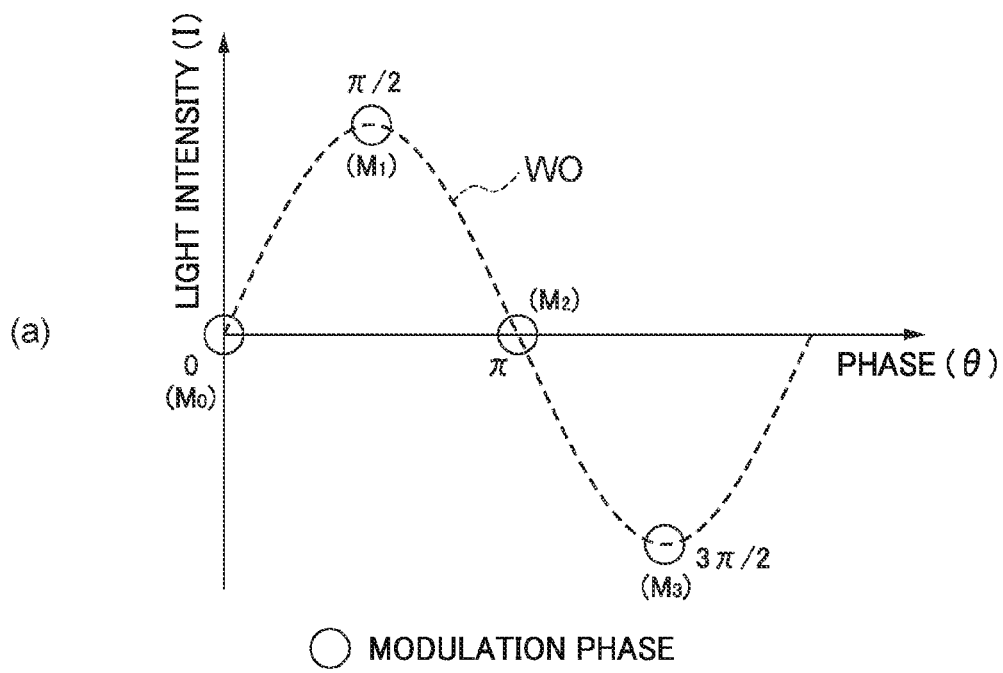
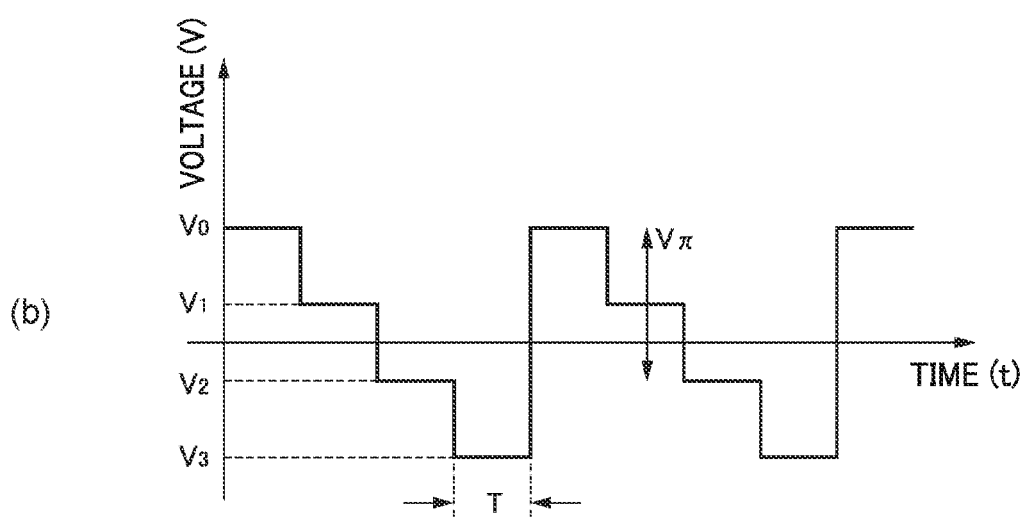

OPTICAL DETECTION DEVICE, OPTICAL DETECTION METHOD, AND PROGRAM

TECHNICAL FIELD

The present invention relates to an optical detection device, an optical detection method, and a program.

BACKGROUND ART

The present invention relates to an optical detection device, an optical detection method, and a program, and in particular, relates to an optical detection device, an optical detection method, and a program employing Raman spectroscopy technology in the analysis of substances. Namely, the present invention is related to an optical detection device in which two or more beams of pulsed laser light are radiated onto a sample, and substances in the sample are analyzed by observing Raman scattered light that is emitted from the sample as a result.

The detection of trace substance using Raman spectroscopy technology is of great importance as a fundamental technology in analytical devices, and there have been many technological developments therein. With recent advances in medical technology, attempts have been made to apply such trace substance detection in medical diagnostic technology, such that there is now also a demand to further increase detection sensitivity for trace substances in the field of medical diagnostic technology.

The coherent anti-Stokes Raman scattering (CARS) method is known as an example of the Raman spectroscopy technology above (Patent Document 1). This is a method in which two or more types of optical pulse are radiated onto a sample, and then coherent anti-Stokes Raman scattered light (CARS light), which has been emitted from the sample due to a non-linear optical process caused by interaction between the optical pulses, is observed.

For example, consider the use of CARS to observe a molecule having energy levels like those illustrated in FIG. 10(a). First, a molecule of the sample at an initial state energy level L1 is excited by the incidence of a first pulsed light (excitation light) having an angular frequency of $\omega 1$, and the energy level of the molecule increases to L3 as indicated by the arrow A. Then, due to causing a second pulsed light (Stokes light) having an angular frequency of $\omega 2$ to be incident to the molecule, the energy level of the molecule falls from L3 to L2 as indicated by the arrow B due to photoemission. Then, due to causing a third pulsed light (probe light) having an angular frequency of $\omega 3$ to also be incident to the molecule, the energy level of the molecule rises from L2 to L4 as indicated by the arrow C, and then falls from L4 to L1 as indicated by the arrow D due to emitting CARS light.

Thus, what is known as a four wave mixing process occurs due to the incidence of the three types of pulsed light, having angular frequencies of $\omega 1$, $\omega 2$, and $\omega 3$, and CARS light having an angular frequency of $\omega 1+\omega 3-\omega 2$ is emitted as a result. CARS light of this sort arises particularly intensely when the frequency difference between the incident pulses, given by $\Delta \omega = \omega 1 - \omega 2$, resonates with the difference in the energy levels of the molecule being observed. When pulsed light that can actually be used in practice is considered, then considering that a strong signal is obtained when $\Delta \omega$ matches a vibrational mode frequency of the molecule, molecules having such vibrational modes can be detected. This method can also be implemented using two types of pulsed light, so as to achieve the detection of CARS light having an angular frequency of $2\omega 1 - \omega 2$ by using the first pulsed light to induce the optical process that would have been caused by the third pulsed light.

FIG. 10(b) illustrates a spectrum SP of pulsed light radiated onto the sample, and a spectrum SC of CARS light emitted as a result of the radiation. Pulsed light corresponding to a portion of the spectrum SP gives rise to Raman scattering, and the spectrum SC of CARS light is emitted with the position of wavelength $\lambda$ shifted by $\Delta\lambda$ toward the short wavelength side. The width $\Delta\lambda$ of the wavelength shift is generally known as the Raman shift, and is sometimes expressed in wavenumbers n (the reciprocal of wavelength $\lambda$, $cm^{-1}$) instead of wavelength. References in the following to the wavelength of pulsed light indicate the central wavelength of the spectrum of pulsed light.

FIG. 11 illustrates a Raman spectroscopy device 80 according to related technology that uses these fundamental principles. The Raman spectroscopy device 80 is configured including two types of laser pulse light sources, these being a first laser pulse light source 82 and a second laser pulse light source 84, an optical system 86 for radiating pulsed light from these light sources onto a single location of a sample 88, and a detection device 90 that detects CARS light emitted by the sample 88 (Patent Document 1, and Non-patent Document 1). Then, for example, CARS light emitted by a specific molecule included in the sample 88 can be selectively detected by changing the wavelengths of the pulsed light emitted from the first laser pulse light source 82 and from the second laser pulse light source 84.

Since CARS light is detected due to molecular vibration, which is an intrinsic property of the molecule in the sample 88, there is no need to stain a trace quantity of a molecule using a marking substance or the like during, for example, the identifying of a trace quantity of a molecule in a living organism. Accordingly, observations can be made without being hindered by the influence of a marking substance, particularly when observing a small molecular compound formed from molecules that are smaller than the molecules of the marking substance. Thus, Raman spectroscopy devices based on the observation of CARS light are particularly advantageous over those employing other methods when observing living organism.

CITATION LIST

Patent Literature

Patent Document 1 Japanese Patent Application Laid-Open (JP-A) No. 2002-107301

Non-Patent Literature

Non-patent Document 1 Journal of Physical Chemistry B105, p. 1277 (2001)
Non-patent Document 2 Applied Physics B 80, p. 243-246 (2005)

SUMMARY OF INVENTION

Technical Problem

A collective measurement of a wideband vibration spectrum is required in order to observe plural vibrational levels or plural types of molecule simultaneously. In order to do so, a wideband light source that includes many light frequencies collected together as one, namely, an ultrashort pulse light source, is required.

However, the frequency resolution of a CARS light signal is lowered as a result of employing a wideband ultrashort pulse light source. This is because it is difficult to obtain an accurate value for the Raman shift since the CARS light signal is also wideband.

Moreover, a non-resonant background simultaneously arises since the peak output (peak power) of the ultrashort pulse is high, and this obscures the CARS light signal subject to observation.

Here, is it known that an optical component referred to above as a non-resonant background is superimposed onto signal light that includes the CARS light, with the CARS light being a resonant component (Non-patent Document 1). FIG. 12(a) illustrates an example of a non-resonant background emission process. First, a molecule of the sample at an energy level L1 of an initial state is excited by incidence of a first pulsed light having an angular frequency of ω1, and the energy level of the molecule increases to a hypothetical level L6 as indicated by the arrow E. Then, the energy level increases further to a hypothetical level L7 as indicated by the arrow F due to causing a second pulsed light having an angular frequency of ω2 to be incident. The energy level of the molecule then falls from the hypothetical level L7 to a hypothetical level L5 as indicated by the arrow G due to causing a third pulsed light having an angular frequency of ω3 to be incident, and then falls from the hypothetical level L5 to level L1 as indicated by the arrow H due to emitting light. Light emitted by transitioning from the hypothetical level L5 to level L1 is the non-resonant background.

FIG. 12(b) illustrates a spectrum SP of incident pulse light, a spectrum SC of CARS light, and respective spectra of a non-resonant background spectrum SN. FIG. 12(b) illustrates five spectra SN to facilitate intuitive understanding; however, in reality, the non-resonant background arises with a continuous spectrum, rather than with discrete spectra. As described above, from the viewpoint of facilitating understanding, explanation has been given for a non-resonant background arising via hypothetical levels L5 to L7, and this is because the actual non-resonant background does not arise via vibrational levels.

When a non-resonant background having a continuous spectrum arises as described above, the CARS light is buried in the non-resonant background. Extraction of CARS light that has been buried in a non-resonant background in this manner is very difficult. Moreover, the non-resonant background acts as noise in the detection of Raman light, and this influence lowers the contrast of the obtained image, and causes negative effects such as shifting or distorting the spectrum.

CARS light generally has a very low intensity since it arises due to non-linear optical effects. Moreover, observation of molecules within living organisms requires that the radiated light intensity of the incident pulsed light be as low as possible to protect the subject of observation, and the CARS light included in the signal light is even weaker in such cases.

As a method for observing weak light buried in noise as explained above, a method exists in which a phase modulation is performed on the incident pulsed light before radiation onto a sample, and lock-in detection is employed to directly extract only the components of the signal light spectrum emitted from the sample that are synchronous with the phase modulation (Non-patent Document 2). However, lock-in detection cannot be applied when a charged coupled device (CCD) is employed as a detector of the signal light. This is due analog-to-digital conversion (A/D) including a direct current (DC) component being required because a CCD is a structure that accumulates charge inside elements. This makes it theoretically impossible for lock-in detection to extract only components that were modulated in the analog signal state.

Moreover, as a method for detecting Raman light without using a lock-in mechanism, a method exists in which random phase modulations are performed on the incident pulsed light before radiation onto the sample, the light intensity of the emitted signal light is acquired plural times, and Raman light is detected from numerical analysis (signal processing) of the plural acquired light intensities. This detection method is a detection method that employs what is known as pseudo-phase sensitive detection.

In relation to the detection method described above, FIG. 13 schematically illustrates a waveform corresponding to one period (from 0 to $2\pi$) of a frequency of incident pulsed light, and positions where phase modulation is performed on the waveform. In this method, phase modulations at random phase positions are performed on incident pulsed light before radiation onto the sample, and the signal on which the phase modulation was performed is approximated as a sinusoidal wave, reconstructed from the signal light scattered in the sample, and extracted.

However, in the detection method described above, several hundred (for example, 500) levels of phase modulation are required in order to detect CARS light with a practical level of sensitivity (FIG. 13 illustrates an example of a case in which phase modulation is performed at 14 phase positions). This detection method therefore requires a great amount of time for measurement, and is insufficient in terms of noise elimination, or sensitivity, since plural random phases are employed.

The present invention has been arrived at in consideration of the circumstances above, and has an objective of establishing a phase sensitive detection mechanism that uses electrical processing, and of providing an optical detection device, an optical detection method, and a program that are capable of detecting faint light at high speed and with high sensitivity using a simple configuration.

Solution to the Problem

An optical detection device according to a first aspect of the present invention includes: a light source section that generates a first pulsed light; a filter section that transmits a second pulsed light formed from a portion of a frequency spectrum exhibited by the first pulsed light, and that reflects a third pulsed light formed from another portion of the frequency spectrum exhibited by the first pulsed light; a phase modulation section that phase modulates the second pulsed light at plural phases; a multiplexing section that produces a fourth pulsed light by multiplexing the third pulsed light with the second pulsed light phase modulated by the phase modulation section; a detector that spectrally disperses and detects scattered light generated by radiating the fourth pulsed light onto a target object; and an extraction section that uses specific calculation processing to synchronize to the phase modulation in the phase modulation section, so as to extract a frequency spectrum of scattered light scattered based on the second pulsed light phase modulated by the phase modulation section from the frequency spectrum of the scattered light detected by the detector.

An optical detection device according to a second aspect of the present invention is the optical detection device according to the first aspect, wherein the plural phases are $\phi$, $\phi+2\pi/3$, and $\phi+4\pi/3$ (where $\phi$ is a fixed phase).

An optical detection device according to a third aspect of the present invention is the optical detection device according to the second aspect, wherein the extraction section calculates I as expressed by the equation below for respective intensities I(φ), I(φ+2π/3), and I(φ+4π/3) at the plural phases of the scattered light detected by the detector, and extracts a frequency spectrum in which the value of I is 0 or a value within an acceptable range of 0:

$$I = \sqrt{\left\{\frac{I\left(\phi + \frac{2\pi}{3}\right) - I\left(\phi + \frac{4\pi}{3}\right)}{\sqrt{3}}\right\}^2 + \left\{\frac{I\left(\phi + \frac{2\pi}{3}\right) + I\left(\phi + \frac{4\pi}{3}\right) - 2I(\phi)}{3}\right\}^2}$$

An optical detection device according to a fourth aspect of the present invention is the optical detection device according to the first aspect, wherein the plural phases are mutually orthogonal.

An optical detection device according to a fifth aspect of the present invention is the optical detection device according to the fourth aspect, wherein the plural phases are φ, φ+π/2, φ+π, and φ+3π/2 (where φ is a fixed phase).

An optical detection device according to a sixth aspect of the present invention is the optical detection device according to the fifth aspect, wherein the extraction section calculates I as expressed by the equation below for respective intensities I(φ), I(φ+π/2), I(φ+π), and I(φ+3π/2) at the plural phases of the scattered light detected by the detector, and extracts a frequency spectrum in which the value of I is 0 or a value within an acceptable range of 0:

$$I = \sqrt{\{I(\phi) - I(\phi+\pi)\}^2 + \left\{I\left(\phi + \frac{\pi}{2}\right) - I\left(\phi + \frac{3\pi}{2}\right)\right\}^2}$$

An optical detection device according to a seventh aspect of the present invention is the optical detection device according to any one of the first aspect to the sixth aspect, wherein: the light source section is a light source that employs an ultrashort pulse laser; and the bandwidth of the frequency spectrum of the second pulsed light is narrower than the bandwidth of the frequency spectrum of the third pulsed light.

An optical detection device according to an eighth aspect of the present invention is the optical detection device according to any one of the first aspect to the seventh aspect, wherein the phase modulation section is a modulator based on electro-optical effects, or a light path length adjustment section that changes a light path length for incident light and emits the incident light.

An optical detection device according to a ninth aspect of the present invention is the optical detection device according to any one of the first aspect to the eighth aspect, wherein the filter section and the multiplexing section are configured by a single bandpass filter that transmits the second pulsed light and the second pulsed light phase modulated by the phase modulation section, and that reflects the third pulsed light.

An optical detection device according to a tenth aspect of the present invention is the optical detection device according to any one of the first aspect to the ninth aspect, wherein the frequency spectrum extracted by the extraction section is a frequency spectrum of coherent anti-Stokes Raman scattered light.

An optical detection method according to an eleventh aspect of the present invention includes: in a filter section, transmitting a second pulsed light formed from a portion of a frequency spectrum exhibited by a first pulsed light emitted by a light source section, and reflecting a third pulsed light formed from another portion of the frequency spectrum exhibited by the first pulsed light; phase modulating the second pulsed light at plural phases using a phase modulation section; producing a fourth pulsed light by using a multiplexing section to multiplex the third pulsed light and the second pulsed light phase modulated by the phase modulation section; spectrally dispersing scattered light generated by radiating the fourth pulsed light onto a target object and detecting the spectrally dispersed scattered light with a detector; and synchronizing to the phase modulation in the phase modulation section by using specific calculation processing, so as to extract a frequency spectrum of scattered light scattered based on the second pulsed light phase modulated by the phase modulation section from the frequency spectrum of the scattered light detected by the detector.

A program according to a twelfth aspect of the present invention controls an optical detection device, the optical detection device includes: a light source section that generates a first pulsed light; a filter section that transmits a second pulsed light formed from a portion of a frequency spectrum exhibited by the first pulsed light, and that reflects a third pulsed light formed from another portion of the frequency spectrum exhibited by the first pulsed light; a phase modulation section that phase modulates the second pulsed light at plural phases; a multiplexing section that produces a fourth pulsed light by multiplexing the third pulsed light with the second pulsed light phase modulated by the phase modulation section; and a detector that spectrally disperses and detects scattered light generated by radiating the fourth pulsed light onto a target object. The program causes a computer to function as an extraction section that uses specific calculation processing to synchronize with the phase modulation in the phase modulation section, so as to extract a frequency spectrum of scattered light scattered based on the second pulsed light phase modulated by the phase modulation section from the frequency spectrum of the scattered light detected by the detector.

Advantageous Effects of Invention

According to the present invention, an optical detection device, an optical detection method, and a program that are capable of detecting faint light at high speed and with high sensitivity using a simple configuration can be provided.

BRIEF DESCRIPTION OF DRAWINGS

FIG. 3(a) is a schematic diagram for explaining modulation phases of phase modulation according to the first exemplary embodiment, and (b) is a graph illustrating a drive voltage applied to an optical modulator

DESCRIPTION OF EMBODIMENTS

Detailed explanation follows regarding exemplary embodiments of the present invention, with reference to the drawings. When phase modulation is performed on pulsed light from a light source in the present invention, the plural modulation phases may be mutually orthogonal or not orthogonal. However, from the viewpoint of facilitating understanding, explanation is first given in the present exemplary embodiments regarding an example of a case in which phase modulation is performed at four orthogonal phases.

First Exemplary Embodiment

In the present invention, a portion of a wideband spectrum of ultrashort pulse light is phase modulated and radiated onto a sample, frequency components that are synchronous with the phase modulated spectrum are extracted from a signal light emitted in the sample, and the extracted frequency components are observed. Namely, the plural orthogonal phases that yield the greatest spectral change are specified for a narrowband pulsed light that is a portion of the wideband spectrum, phase modulation is performed thereon, and the spectra of the respective modulation phases are integrated to improve the contrast of the signal. Note that "orthogonal" in the present exemplary embodiment is used with the ordinary meaning, namely, that integrating the product of the two signals gives a result of 0.

Figure 1:
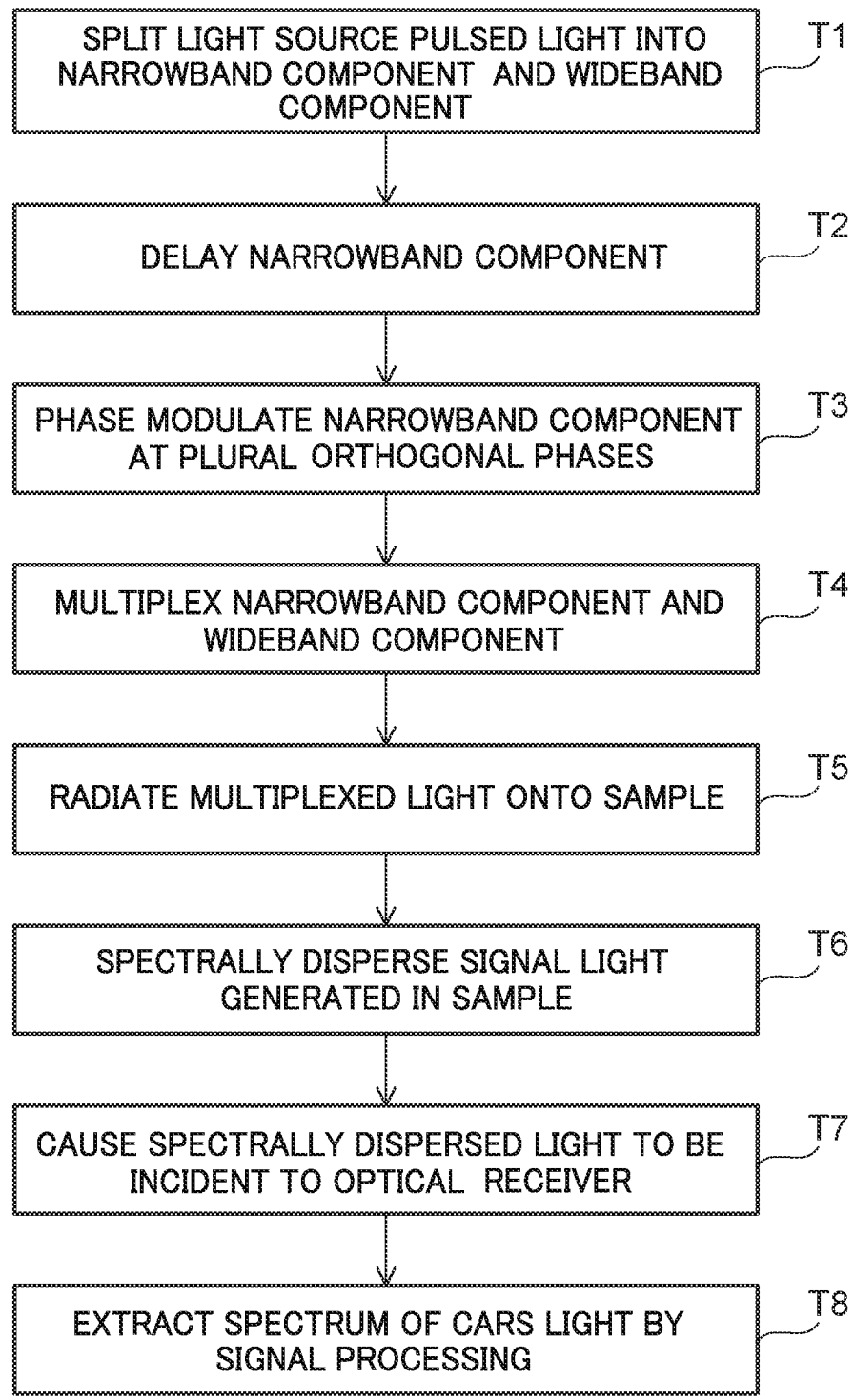
FIG. 1 is a diagram for explaining a procedure for an optical detection method according to the exemplary embodiments.

More specific explanation regarding the general outline of the present invention follows, with reference to FIG. 1. FIG. 1 illustrates a procedure for an optical detection method according to the present invention, with this same figure illustrating an example of a case in which CARS light emitted in a sample is extracted as spectral information.

As illustrated in FIG. 1, first, in procedure T1, pulsed light of a light source is split into a pulsed light (first pulsed light) having a narrowband component and a pulsed light (second pulsed light) having a wideband component.

In the next procedure T2, the first pulsed light is delayed with respect to the second pulsed light. The first pulsed light is delayed in order to selectively eliminate signal light that has a short relaxation time. The delay can, for example, effectively eliminate signals arising from water, which is a primary source of noise in living organisms.

In the next procedure T3, phase modulation is performed on the first pulsed light that was delayed in procedure T2, at plural predetermined orthogonal phases.

In the next procedure T4, the phase modulated first pulsed light and the second pulsed light are multiplexed.

In the next procedure T5, the multiplexed light is radiated onto the sample.

In the next procedure T6, signal light emitted in the sample is spectrally dispersed.

In the next procedure T7, the spectrally dispersed signal light is caused to be incident to an optical receiver and converted into an electrical signal.

In the next procedure T8, specific signal processing is executed on the electrical signal in order to extract a spectrum of CARS light.

The spectrum of CARS light reflected by vibrations of molecules included in the sample can be obtained by the procedure above.

Figure 2:
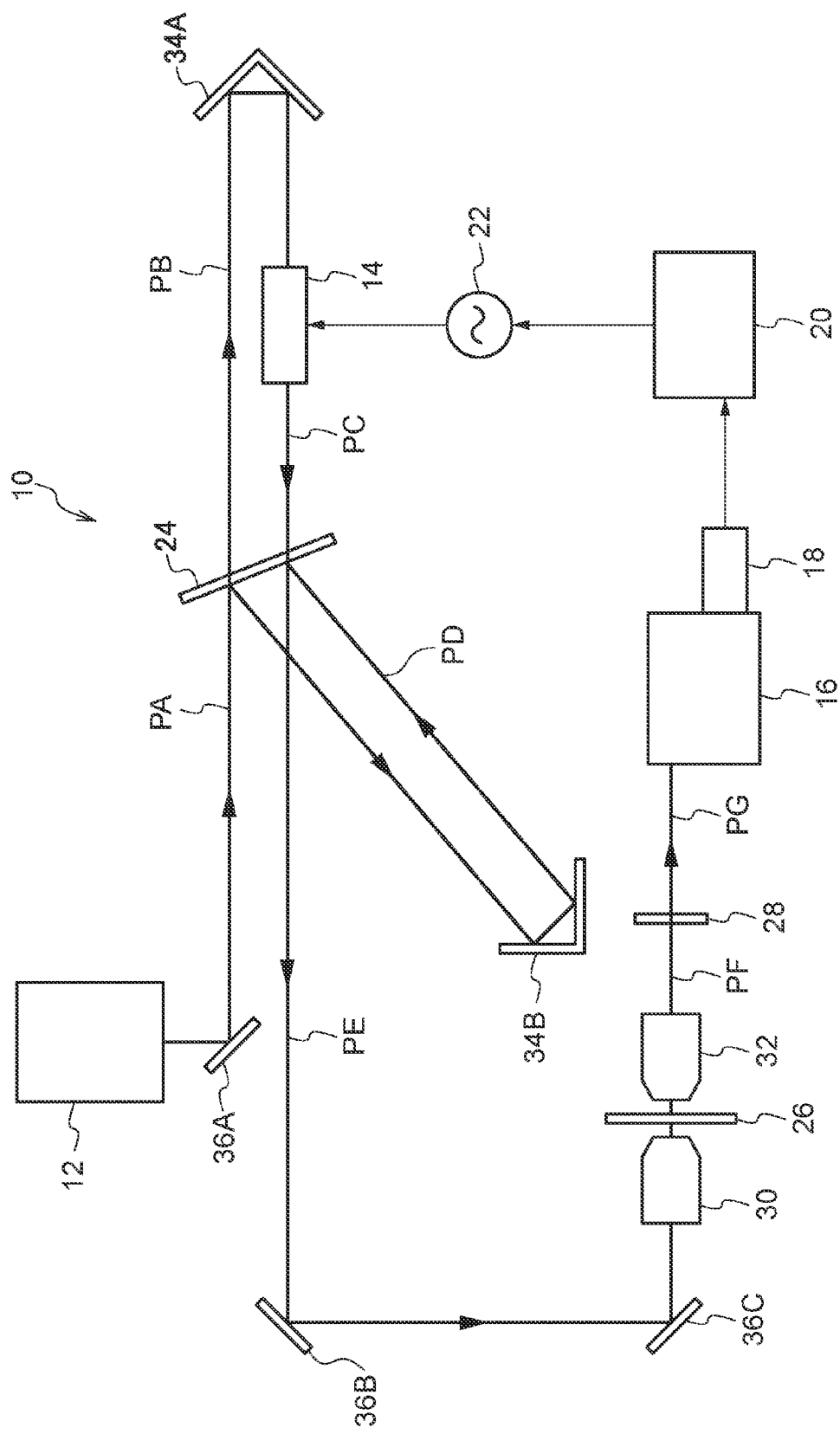
FIG. 2 is a schematic diagram illustrating an example of a configuration of an optical detection device according to a first exemplary embodiment.

FIG. 2 illustrates an optical detection device 10 according to the present exemplary embodiment. The optical detection device 10 is configured including a light source 12, an optical modulator 14, a spectroscope 16, an optical receiver 18, a controller 20, a signal generator 22, a bandpass filter 24, a shortpass filter 28, objective lenses 30, 32, retroreflectors 34A, 34B, and reflectors 36A, 36B, 36C.

In the optical detection device 10, the light source 12 is a light source that respectively emits light corresponding to the excitation light, the Stokes light, and the probe light in the Raman scattering process. In the optical detection device 10 according to the present exemplary embodiment, an ultrashort pulse laser that emits wideband pulsed light is employed as the light source 12.

The bandpass filter 24 is a narrowband bandpass filter that transmits a portion of pulsed light PA emitted from the light source 12 as narrowband first pulsed light PB, and reflects other portions as wideband second pulsed light PD. Moreover, the bandpass filter 24 according to the present exemplary embodiment also functions so as to multiplex phase modulated first pulsed light PC with second pulsed light PD that has been sent back by the retroreflector 34B, and obtains a pulsed light PE to be radiated onto a sample 26.

Explanation is given in the present exemplary embodiment regarding an example of a mode in which the bandpass filter 24 functions so as to split and multiplex the first pulsed light PC and the second pulsed light PD; however, there is no limitation thereto, and configuration may be made such that separate elements are employed therefor. In such cases, an ordinary half mirror may be employed as the element that multiplexes.

The retroreflector 34A is a location where incident first pulsed light PB that has been split by the bandpass filter 24, is sent back in the direction of incidence. Reflectors disposed at right angles to each other are employed in the present exemplary embodiment; however, there is no limitation thereto, and, for example, a right angle prism may be employed.

The optical modulator 14 is a modulator that performs specific phase modulations on the first pulsed light PB that has been sent back by the retroreflector 34A, and thereby produces the modulated first pulsed light PC. In the present exemplary embodiment, an explanation is given regarding an example of a mode that employs an LN (lithium niobate; $LiNbO_3$) modulator that modulates the phase of light using an electro-optical effect, as an example of the optical modulator 14; however, there is no limitation thereto. For example, a mode may be adopted that employs a configuration such as a reflector equipped with a drive mechanism or the like to mechanically delay phases of light.

The signal generator 22 is a signal generator that generates an electrical signal for performing phase modulation by changing the driving voltage of the optical modulator 14. The output of the signal generator 22 may be connected to the optical modulator 14 via a drive circuit, omitted from illustration, in some cases.

The objective lens 30 is a lens that focuses the pulsed light PE multiplexed by the bandpass filter 24, and radiates the focused light onto the sample 26. The objective lens 32 is a lens that focuses the pulsed light PF (including excitation light and the like alongside the CARS light), this being the signal light generated in the sample, and guides the focused light to the spectroscope 16.

The position at which the pulsed light PE is radiated onto the sample 26 may be changed (scanned) by moving at least one out of the objective lens 30 or the sample 26. A drive mechanism capable of moving at least one out of the objective lens 30 or the sample 26 within the plane perpendicular to the page, such as a drive mechanism employing piezo elements, may be provided in such cases.

The shortpass filter 28 is a long wavelength cut-off filter that facilitates extraction of the CARS light by eliminating, from the pulsed light PF, excitation light components (light simply transmitted through the sample 26), which have light intensities far greater than that of the CARS light, thereby producing a pulsed light PG. Note that the eliminated excitation light may be just part of the excitation light. Moreover, the shortpass filter 28 is appropriately provided according to the magnitude of the excitation light, and is not always necessary.

The spectroscope 16 is the location where the pulsed light PG is spectrally dispersed, and where the spectrally dispersed light is guided to the optical receiver 18, and may be configured using a general spectrometer without any particular limitations.

The optical receiver 18 is the location where light including the spectrally dispersed CARS light is received, and, as an example, employs a CCD in the present exemplary embodiment. The optical receiver 18 is not limited to a CCD, and may, for example, employ another optical reception element such as a photomultiplier tube or a photodiode.

The controller 20 is where signal processing to extract CARS light frequency components from the pulsed light PG, which includes the CARS light generated by the sample 26, is performed, and is also where waveform control and the like is performed on a drive voltage generated by the signal generator 22 for phase modulation by the optical modulator 14. The controller 20 may be configured using a general personal computer or the like.

The reflectors 36A, 36B, 36C are mirrors for switching the light path.

Next, more specific explanation follows regarding the phase modulation performed by the optical modulator 14 according to the present exemplary embodiment, with reference to FIG. 3.

In the optical detection device 10 according to the present exemplary embodiment, the four phases that yield the greatest spectral changes in the narrowband pulsed light PB are specified for the narrowband pulsed light PB that is a portion of the wideband spectrum, and phase modulation is performed thereon. Then, the contrast of the signal is increased by integrating the light intensity I for each of the modulation phases. In the present exemplary embodiment, four orthogonal phases, namely, the four phases $0$, $\pi/2$, $\pi$, and $3\pi/2$ with respect to a reference phase of 0, are employed as the four phases.

Namely, as illustrated in FIG. 3(*a*), in the present exemplary embodiment, phase modulation is performed on one cycle of a waveform WO of light of the pulsed light PB at a reference phase position $M_0$ of phase 0, a phase position $M_1$ of phase $\pi/2$, a phase position $M_2$ of phase $\pi$, and a phase position $M_3$ of phase $3\pi/2$.

FIG. 3(*b*) illustrates an example of a drive voltage waveform applied to the optical modulator 14 when performing the phase modulation described above, and as illustrated in this same figure, the present exemplary embodiment employs a stepped drive voltage waveform. Since the optical modulator 14 according to the present exemplary embodiment employs an LN modulator, a voltage signal is employed as the drive signal of the optical modulator.

In FIG. 3(*b*), $V_0$, $V_1$, $V_2$, and $V_3$ represent drive voltages that are respectively applied at the phase positions $M_0$, $M_1$, $M_2$, and $M_3$ of FIG. 3(*a*), and phase changes at $0$, $\pi/2$, $\pi$, and $3\pi/2$ are thus respectively applied to the pulsed light PB. $V_\pi$ illustrated in FIG. 3(*b*) indicates the half-wave voltage of the LN modulator, namely, the drive voltage that applies a phase change of $\pi$ to the light signal. Moreover, in the optical detection device 10 according to the present exemplary embodiment, as an example, the duration T of each drive voltage is 1 ms (millisecond).

Note that in the present exemplary embodiment, it is sufficient for the phase modulation described above to preserve the relative relationship between the four phases (namely, phase differences of $\pi/2$), and the absolute value of the phases is not an issue.

In the optical detection device 10 according to the present exemplary embodiment, the drive voltage of the optical modulator 14 described above is supplied from the signal generator 22 (or from the signal generator 22 via a drive circuit, omitted from illustration), and the voltage waveform generated by the signal generator 22 is controlled by the controller 20. Conditions related to phase modulation performed in the optical modulator 14, for example, the number of phase modulations, the modulation phase of each phase position, and the drive voltage applied for each phase modulation, may be stored in a storage means such as read only memory (ROM) or non-volatile memory (NVM), omitted from illustration, provided in the controller 20.

Moreover, although explanation has been given in the present exemplary embodiment regarding an example in which a stepped waveform serves as the waveform of the drive voltage applied to the optical modulator 14, there is no limitation thereto, and, for example, a pulse waveform having peak values that are the respective driving voltages ($V_0$, $V_1$, $V_2$, $V_3$) may be employed.

Figure 4:
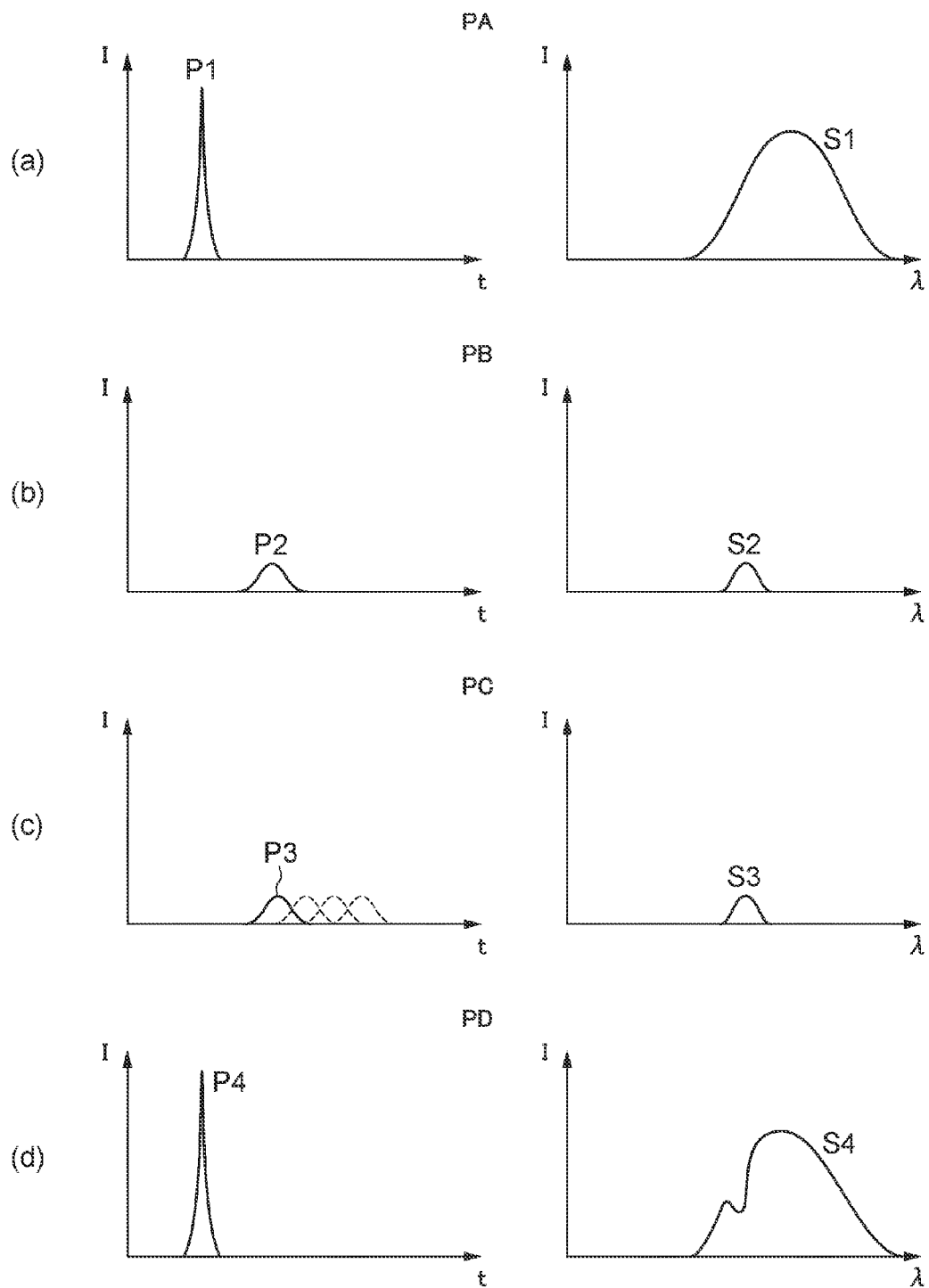
FIG. 4 shows some of the diagrams illustrating waveforms and spectra of respective light signals of an optical detection device according to the first exemplary embodiment.
Figure 5:
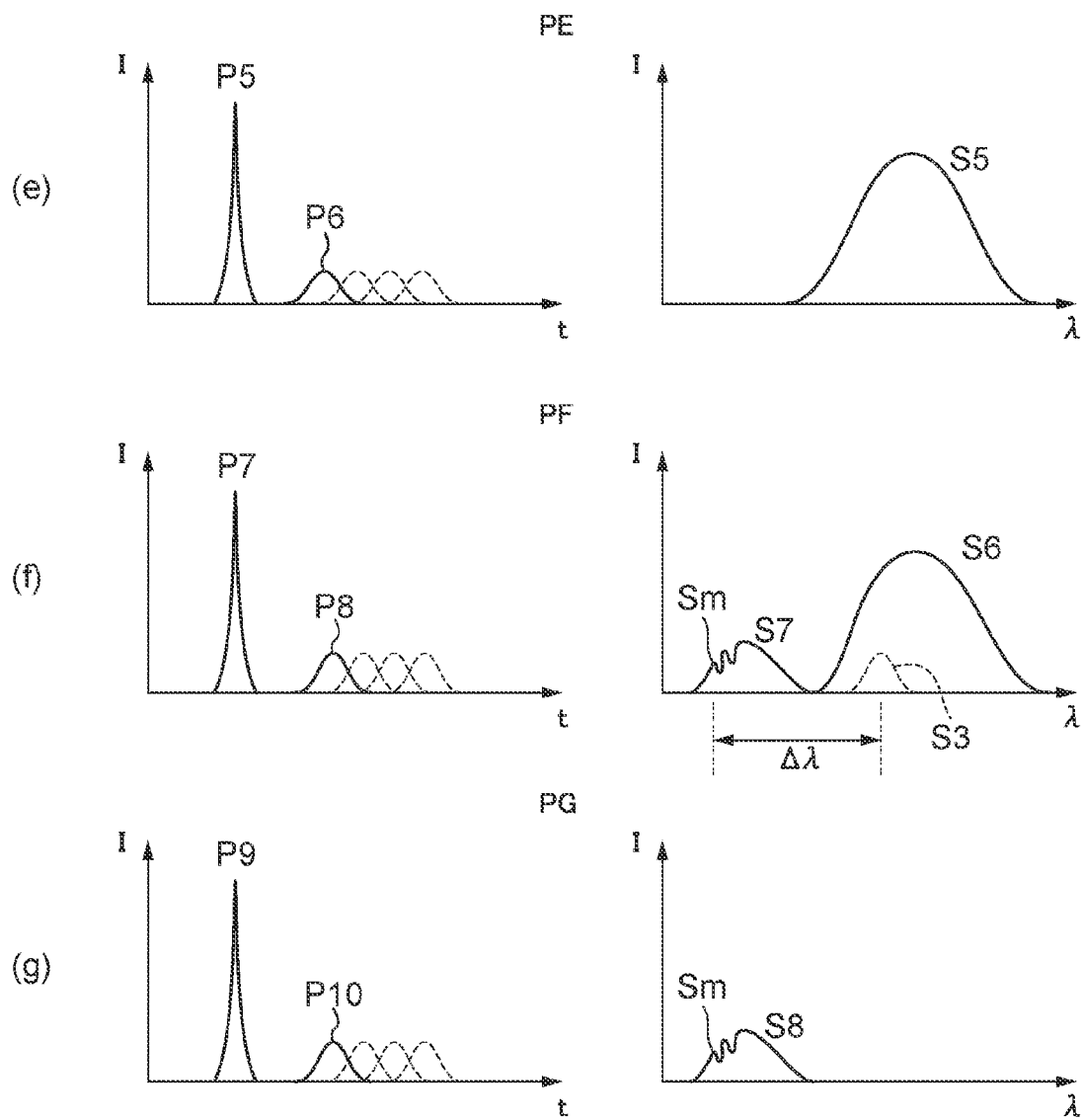
FIG. 5 shows some of the diagrams illustrating waveforms and spectra of respective light signals of an optical detection device according to the first exemplary embodiment.

Next, explanation follows regarding pulsed waveforms and spectra of the pulsed light PA to the pulsed light PG described above, with reference to FIG. 4 and FIG. 5. FIG. 4(*a*) to FIG. 4(*d*) respectively illustrate pulsed waveforms (the horizontal axis is time t; the vertical axis is light intensity I) and spectra (the horizontal axis is wavelength $\lambda$; the vertical axis is light intensity I) of the pulsed light PA to the pulsed light PD. Moreover, FIG. 5(*e*) to FIG. 5(*g*) respectively illustrate pulsed waveforms and spectra of the pulsed light PE to the pulsed light PG.

As illustrated in FIG. 4(*a*), the pulsed light PA (the light emitted from the light source 12) according to the present exemplary embodiment has a wideband spectrum S1, and is a light pulse P1 that is an ultrashort pulsed laser having a pulse width on the order of femtoseconds. More specifically, a Ti:sapphire laser having a central wavelength of approximately 800 nm, a pulse width on the order of femtoseconds (for example, 10 fs), and a bandwidth of 100 nm (1600 cm$^{-1}$) is employed as an example of the light source 12.

As illustrated in FIG. 4(b), the pulsed light PA is transmitted by the bandpass filter 24 as the pulsed light PB, and after being split, becomes a light pulse P2 having a narrowband spectrum S2. In the optical detection device 10 according to the present exemplary embodiment, the bandwidth of the pulsed light PB is, as an example, approximately 4 nm (60 cm$^{-1}$).

FIG. 4(c) illustrates a state in which the pulsed light PB has been modulated at plural phases by the optical modulator 14, and output as the pulsed light PC. As illustrated in FIG. 4(c), when the pulsed light P3 has been phase modulated at plural phases, it becomes possible to measure the light intensity I at a number of offset phases of the number of phase modulations (four in the present exemplary embodiment) as described below. Note that the spectrum S3 of the light pulse P3 is essentially the same as the spectrum S2 described above, except for minute fluctuations in the spectrum caused by the phase modulation in the optical modulator 14.

FIG. 4(d) illustrates pulsed light PD that has been reflected by the bandpass filter 24 and split, and the pulsed light PD is configured by a light pulse P4 having a wideband spectrum S4. The spectrum S4 is a spectrum given by subtracting a portion corresponding to the spectrum S3 from the spectrum S1.

When the pulsed light PC and the pulsed light PD described above have been multiplexed by the bandpass filter 24, the light pulse P5 and the light pulse P6, having a spectrum S5, are obtained as illustrated in FIG. 5(e). These light pulses configure the pulsed light PE.

In the optical detection device 10 according to the present exemplary embodiment, the pulsed light PC described above acts as both the excitation light and the probe light, and the pulsed light PD acts as the stokes light.

When the pulsed light PE has been radiated onto the sample 26, signal light including spectra S6 and S7, as illustrated in FIG. 5(f), is emitted as the pulsed light PF. The spectrum S7 is a spectrum corresponding to CARS light, and the spectrum S6 is a spectrum primarily corresponding to the excitation light. Moreover, as illustrated in FIG. 5(f), a spectrum marker Sm is included in the spectrum S7. Although a single spectrum S7 is illustrated in FIG. 5(f), in practice, plural CARS lights are emitted simultaneously since excitation is performed using wideband light in the optical detection device 10 according to the present exemplary embodiment.

In the present exemplary embodiment, "spectrum marker" refers to a fluctuating portion of the spectrum of the signal light generated as a result of interference between the CARS light emitted from the sample 26 and the non-resonant spectrum, and is caused by the phase modulation by the optical modulator 14. The form of the fluctuation of the fluctuating portion of the spectrum is what is known as a sinusoidal waveform, and when the phase of the pulsed light PB has been shifted as illustrated in FIG. 4(c), the phase of the sinusoidal waveform is shifted in the direction of the wavelength λ axis. In the present exemplary embodiment, the fluctuating portion, namely, the spectrum marker, is employed as an indicator of the Raman shift. Namely, a wavelength difference Δλ of from the central wavelength of the spectrum S3 included in the spectrum S6 indicated by the dashed line in FIG. 5(f) to the wavelength of the spectrum marker Sm portion, corresponds to the Raman shift.

Thus, in the optical detection device 10 according to the present exemplary embodiment, the frequency resolution can be increased by marking a narrowband component that includes the CARS light. Although a single spectrum marker Sm is illustrated in FIG. 5(f), in practice, plural spectrum markers Sm will be generated corresponding to plural CARS lights.

When the pulsed light PF has passed through the shortpass filter 28, a CARS light spectrum S8, as illustrated in FIG. 5(g), is primarily extracted. The CARS light spectrum S8 includes the spectrum marker Sm, from which a specific portion of the spectrum S6 that is primarily the spectrum of the excitation light has been subtracted. In practice, a spectrum of a non-resonant background, described above, is also generated surrounding the spectrum S8, and some of this spectrum also passes through the shortpass filter 28 at the same time.

Figure 6:
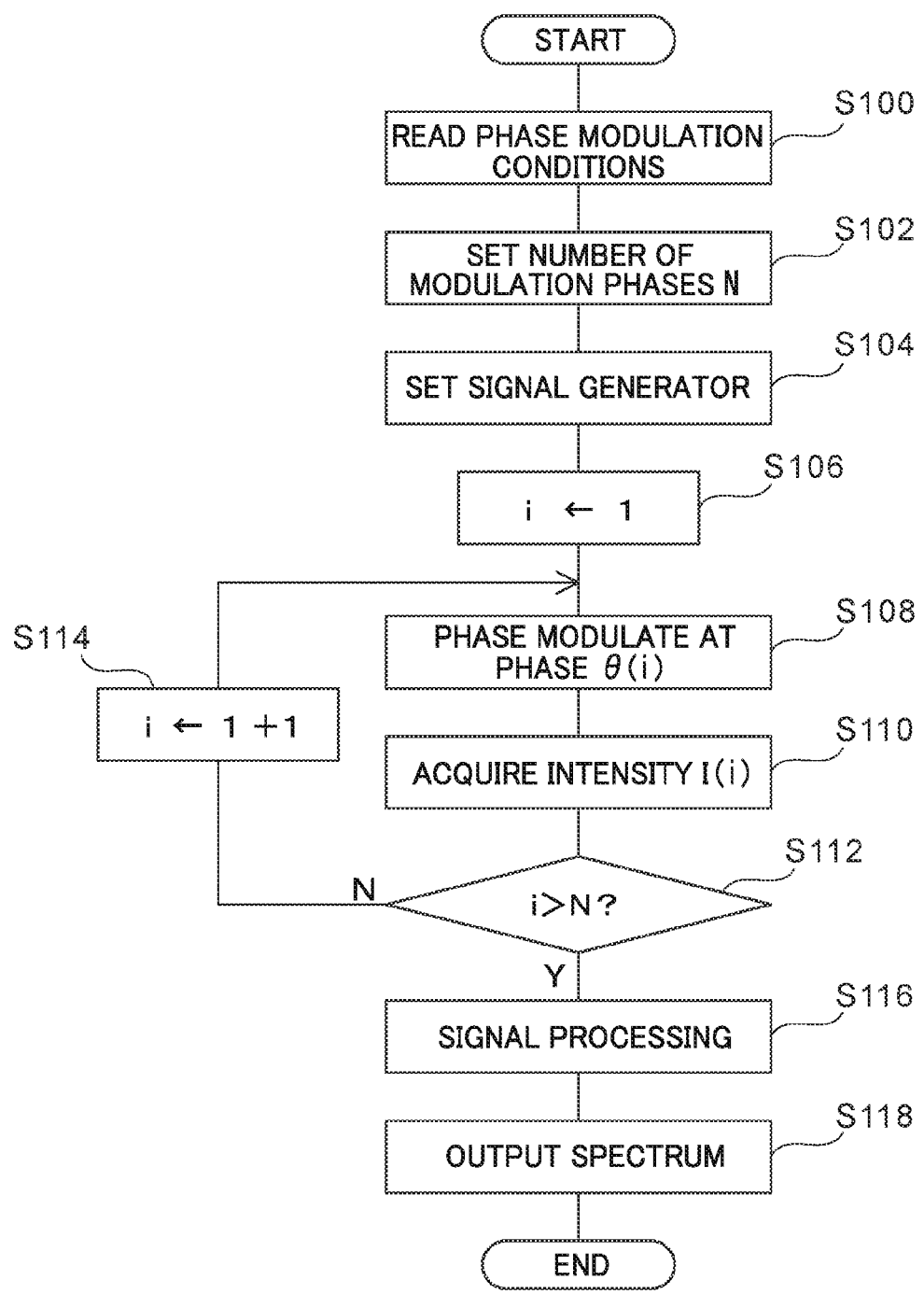
FIG. 6 is a flowchart illustrating a flow of processing of an optical detection processing program according to the exemplary embodiments.

Next, explanation follows regarding optical detection processing executed by the optical detection device 10 according to the present exemplary embodiment, with reference to FIG. 6. FIG. 6 is a flowchart illustrating a flow of processing of an optical detection processing program according to the present exemplary embodiment.

In the optical detection device 10 according to the present exemplary embodiment, the processing illustrated in FIG. 6 instructs, via the controller 20 or the like, the start of optical detection, such that a CPU, omitted from illustration, provided inside the controller 20 reads the optical detection processing program, which is stored in a storage means such as ROM, and executes the optical detection processing program.

Moreover, although explanation has been given in the present exemplary embodiment regarding an example of a mode in which the optical detection processing program is pre-stored in a storage means such as ROM, there is no limitation thereto. For example, a mode in which the optical detection processing program is provided in a state stored on a portable storage medium readable by a computer, a mode may be applied in which the optical detection processing program is distributed by wire or wirelessly through a communication means, or the like.

Moreover, although the optical detection processing is implemented by executing the program with a software configuration that employs a computer in the present exemplary embodiment, there is no limitation thereto. For example, the optical detection processing may be implemented by a hardware configuration employing an application specific integrated circuit (ASIC), or by a combination of a hardware configuration and a software configuration.

As illustrated in FIG. 6, first, at step S100, phase modulation conditions (such as the number of modulation phases, the modulation phase of each modulation position, and the drive voltage applied for each phase modulation) are read into the optical modulator 14 from a storage means such as ROM or NVM, omitted from illustration, provided in the controller 20.

At the next step S102, N modulation phases (N=4 in the present exemplary embodiment) are set based on the phase modulation conditions read at step S100, and at the next step S104, a drive voltage, a driving waveform, or the like, is set in the signal generator 22 for driving the optical modulator 14.

At the next step S106, a counter for the N modulation phases, i, is set to 1. At the next step S108, phase modulation is performed at phase θ(i) in the optical modulator 14, and at the next step S110, after modulating at phase θ(i), the light intensity I(i) is acquired.

At the next step S112, determination is made as to whether or not the counter i is greater than N, and the counter i is incremented by 1 at step S114 in cases in which negative determination was made, processing returns to step S108, and phase modulation continues at phase θ(i+1).

However, processing transitions to step S116 in cases in which positive determination was made at step S112, and signal processing is performed to extract a CARS light spectrum based on the light intensity I(i) acquired by modulation at each phase θ(i). The signal processing to extract the CARS light spectrum is performed in synchronization with the phase modulation in the optical modulator 14.

The signal processing is performed based on processing represented by Equation (1) below.

$$I = \sqrt{\{I(0) - I(\pi)\}^2 + \left\{I\left(\frac{\pi}{2}\right) - I\left(\frac{3\pi}{2}\right)\right\}^2} \quad \text{Equation (1)}$$

More specifically, a spectrum in which the value of I in Equation (1) above is 0, or a value within an acceptable range of 0, is identified from the signal light spectrum, a portion of the signal light spectrum corresponding to the spectrum marker Sm is extracted, and a spectrum is calculated. The spectrum calculated at step S118 is then output. The optical detection processing program subsequently ends.

According to the present signal processing, the non-resonant background components can be subtracted out irrespective of the intensity or the spectrum waveform of the non-resonant background. Accordingly, the influence of the non-resonant background can be eliminated from the emitted CARS light, enabling a high sensitivity optical detection device to be implemented.

The acceptable range mentioned above may be set in advance according to a simulation or an experiment employing actual equipment or the like, for example, and may be stored in ROM, NVM, or the like, omitted from illustration, of the controller 20.

Although explanation has been given in the exemplary embodiment described above regarding an example of a case in which a cycle of measurement for the four phases was executed once, there is no limitation thereto, and the cycle may be executed plural times. The S/N ratio increases with each executed cycle.

Figure 7:
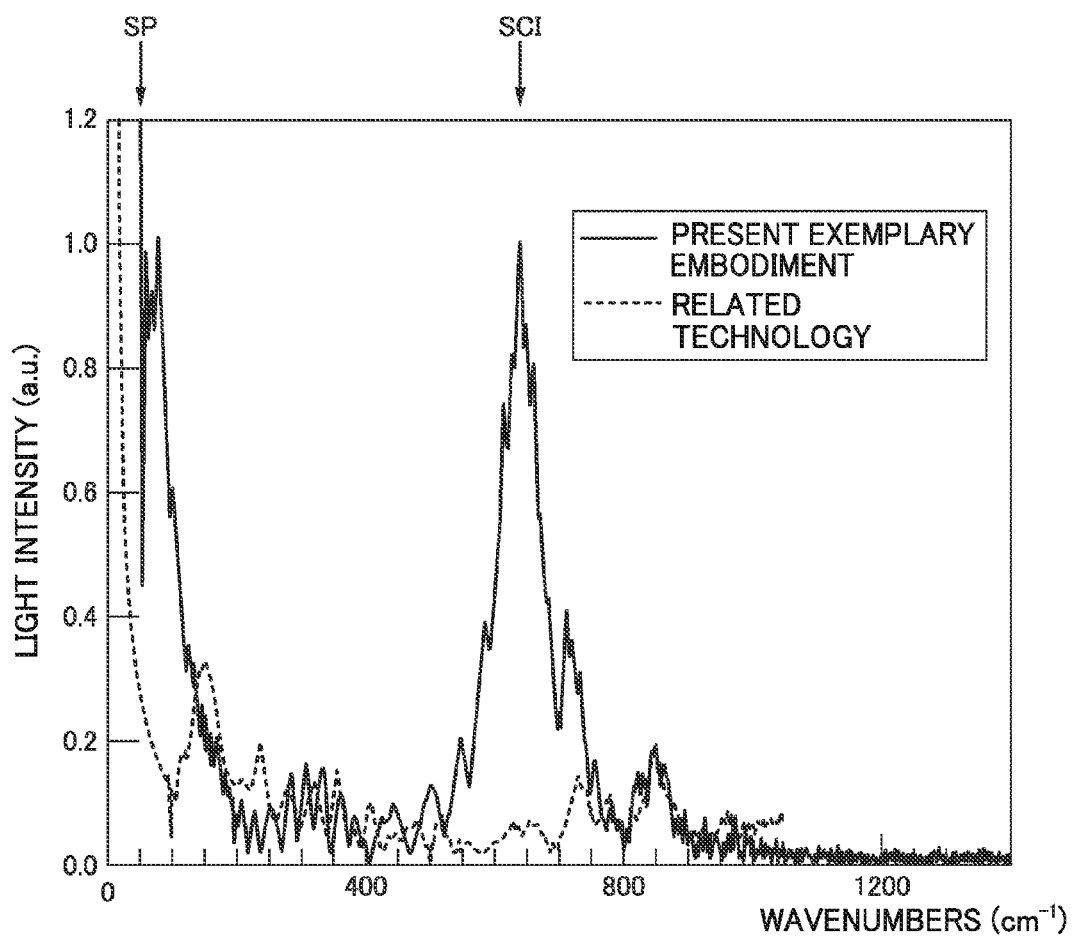
FIG. 7 is a graph illustrating an example in an optical detection device according to the first exemplary embodiment.

Next, explanation follows regarding an example of the optical detection device 10, according to the present exemplary embodiment, with reference to FIG. 7. FIG. 7 illustrates, for the same sample, a comparison between optical detection results for CARS light by the optical detection device 10 according to the present exemplary embodiment, and optical detection results for CARS light by an optical detection device according to related technology that uses random phase modulations as described above.

In the example illustrated in FIG. 7, the following conditions were employed for both the optical detection device according to the present exemplary embodiment and the optical detection device according to related technology.
light source 12 (pulsed light PA): wavelength 800 nm, pulse width 10 fs, bandwidth 125 nm (2000 cm$^{-1}$)
narrowband pulsed light (pulsed light PB): wavelength 777 nm, pulse width 0.6 ps, bandwidth 4 nm
sample: dropped preparation of neat isoflurane In FIG. 7, the horizontal axis indicates wavenumbers, and the amount of shift in wavenumbers with respect to the wavenumber of the excitation light is illustrated. Moreover, the vertical axis represents light intensity (in a.u.). In the example illustrated in FIG. 7, the number of integrated measurements by the optical detection device according to related technology (namely, the number of random modulation phases) is 500.

In FIG. 7, the spectrum indicated by SCI is a CARS light spectrum of characteristic molecular vibrations of isoflurane. It is apparent that although the spectrum of the CARS light is mostly unobservable in the optical detection device according to related technology, the optical detection device according to the present exemplary embodiment enables the CARS light spectrum to be observed clearly. Note that the spectrum indicated by SP in FIG. 7 is the excitation light spectrum.

As described in detail above, the optical detection device, the optical detection method, and the program according to the present exemplary embodiment enable an optical detection device, an optical detection method, and a program that are capable of detecting faint light at high speed and with high sensitivity to be provided by a simple configuration. The optical detection device, the optical detection method, and the program according to the present exemplary embodiment can exhibit an advantageous effect of being uninfluenced, for example, by temperature drift in the characteristic operating point of the LN modulator as long as the relative phase relationship in the phase modulation can be determined.

Second Exemplary Embodiment

Figure 8:
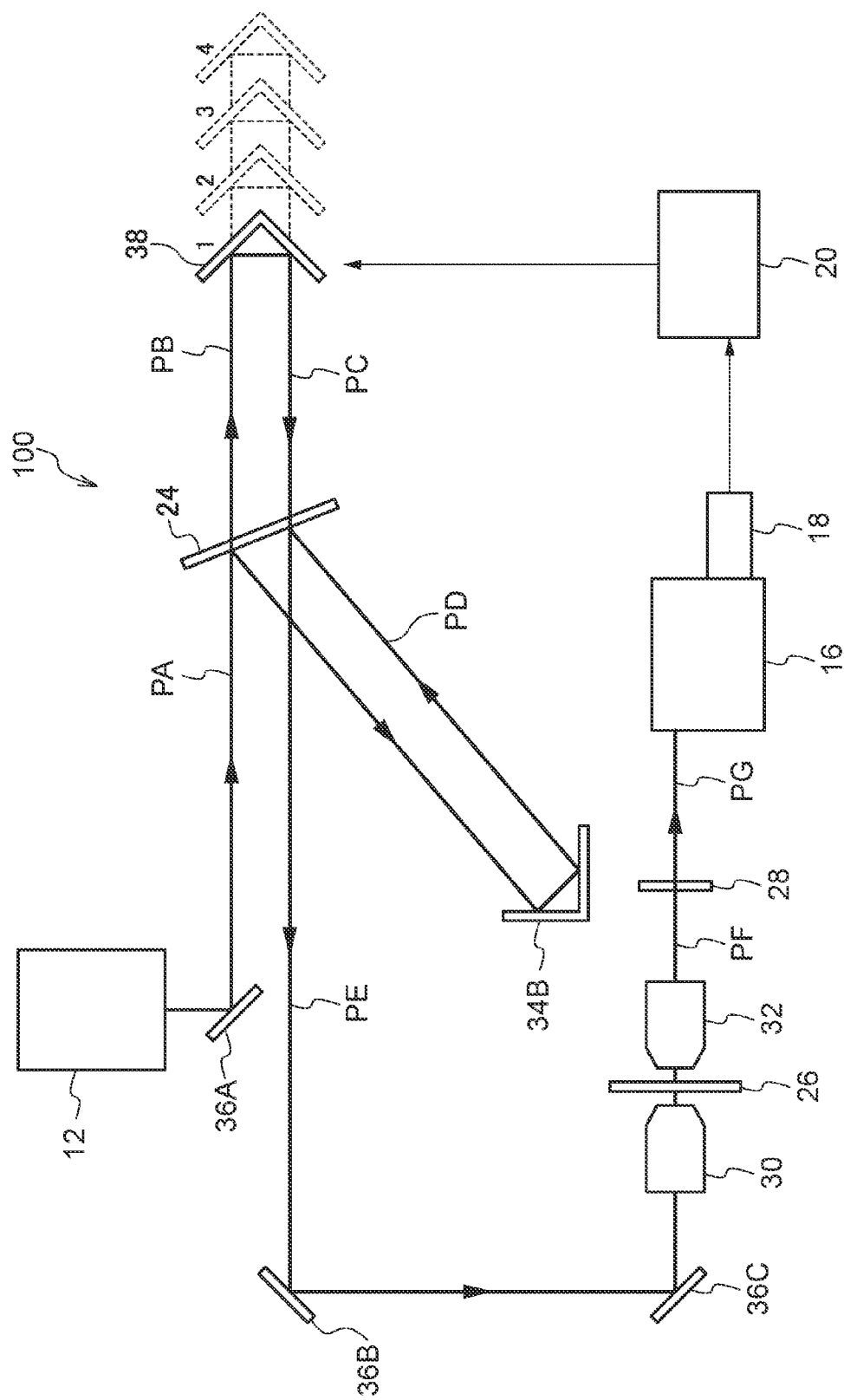
FIG. 8 is a schematic configuration diagram illustrating an example of a configuration of an optical detection device according to a second exemplary embodiment.

Next, explanation follows regarding an optical detection device 100 according to the present exemplary embodiment, with reference to FIG. 8. The optical detection device 100 according to the present exemplary embodiment is obtained by changing the method of phase modulating the first pulsed light PB in the optical detection device 10 according to the first exemplary embodiment. The same reference numerals are therefore appended to configuration similar to that of FIG. 2, and explanation thereof is omitted.

Although an LN modulator was employed as the optical modulator 14 in the optical detection device 10, the optical detection device 100 employs a drive mechanism-equipped retroreflector 38. As illustrated in FIG. 8, in the optical detection device 100, the controller 20 performs phase modulation by disposing the drive mechanism-equipped retroreflector 38 at plural positions corresponding to specific modulation phases (four positions in the present exemplary embodiment), via a drive mechanism, omitted from illustration.

In FIG. 8, positions corresponding to specific phase modulations are indicated by numerals 1 to 4 appended to the drive mechanism-equipped retroreflector 38, and these positions corresponds to respective phase positions $M_0$ to $M_3$, of FIG. 3. Namely, the positions of the drive mechanism-equipped retroreflector 38 appended with the numerals 1 to 4 respectively correspond to modulation phases 0, π/2, π, and 3π/2. Thus, similarly to in the optical detection device 10 of FIG. 2, in the optical detection device 100, it is also sufficient to preserve relative position relationships between the four phases, and the absolute value of the phases is not an issue. At each section in the optical detection device 100, the waveforms and spectra of the pulsed light PA to the pulsed light PG is similar to FIG. 4 and FIG. 5.

The optical detection processing program according to the present exemplary embodiment is also essentially similar to the optical detection processing program according to the first exemplary embodiment illustrated in FIG. 6; however it differs somewhat in step S104. Namely, in the optical detection processing program according to the present exemplary embodiment, instead of setting the signal generator 22 at step S104, the drive mechanism of the drive mechanism-equipped retroreflector 38 is set, namely, the position of the drive mechanism-equipped retroreflector 38 etc. corresponding to each of the modulation phases is set. Then, based on the set position of the drive mechanism-equipped retroreflector 38, phase modulation is performed at phase θ(i) at step S108 similarly to in the first exemplary embodiment, and the light intensity I(i) is acquired at step S110.

As described above, the optical detection device, the optical detection method, and the program according to the present exemplary embodiment also enable an optical detection device, an optical detection method, and a program that are capable of detecting faint light at high speed and with high sensitivity to be provided by a simple configuration.

Third Exemplary Embodiment

The present exemplary embodiment is a mode that generalizes the number of modulation phases N, out of the phase modulation conditions when performing signal processing to extract the CARS light spectrum, in each of the exemplary embodiments described above. Moreover, the present exemplary embodiment is a mode that can also be applied to cases in which phase modulation is performed at plural non-orthogonal phases.

First, a general representation of the light intensity $I(\phi_N)$ of the resonant signal measured by the optical receiver is given by Equation (2) with respect to plural phases $\Phi+\phi_N$.

$$I(\varnothing_N) = I\cos(\Phi+\varnothing_N) + I_{NRB} \quad \text{Equation (2)}$$

Herein, N is an index representing different modulation phases, $\Phi$ is an unknown fixed phase, and $I_{NRB}$ is the intensity of the non-resonant background.

For example, when the number of modulation phases N is 4, Equation (1) of the exemplary embodiments described above can be derived from Equation (2) as follows.

Equations (3) are obtained by substituting $\phi_N=0, \pi/2, \pi, 3\pi/2$ into Equation (2).

$$I(0) = I\cos\Phi + I_{NRB} \quad \text{Equations (3)}$$
$$I\left(\frac{\pi}{2}\right) = -I\sin\Phi + I_{NRB}$$
$$I(\pi) = -I\cos\Phi + I_{NRB}$$
$$I\left(\frac{3\pi}{2}\right) = I\sin\Phi + I_{NRB}$$

Equations (4), given below, are obtained by eliminating $I_{NRB}$ from Equations (3).

$$I(0) - I(\pi) = 2I\cos\Phi \quad \text{Equations (4)}$$
$$I\left(\frac{\pi}{2}\right) - I\left(\frac{3\pi}{2}\right) = 2I\sin\Phi$$

Both sides of each Equation (4) are then raised to the power 2 so that the unknown fixed phase $\Phi$ can be eliminated, and Equation (1) is obtained similarly to Equation (5), given below, by adding Equations (4) together and taking the square root thereof.

$$2I = \sqrt{\{I(0) - I(\pi)\}^2 + \left\{I\left(\frac{\pi}{2}\right) - I\left(\frac{3\pi}{2}\right)\right\}^2} \quad \text{Equation (5)}$$

Note that the coefficient of ½ is omitted in Equation (1) since applying the coefficient to the entire right hand side of Equation (5) is unsubstantial.

In the present invention, the light intensity $I(\phi_N)$ can also be theoretically derived when the number of modulation phases N is 3 since there are 3 unknown amounts: I, $\Phi$, and $I_{NRB}$. As an example, Equations (6), given below, are obtained when $\phi_N=0, 2\pi/3, 4\pi/3$.

$$I(0) = I\cos\Phi + I_{NRB} \quad \text{Equations (6)}$$
$$I\left(\frac{2\pi}{3}\right) = I\cos\left(\Phi + \frac{2\pi}{3}\right) + I_{NRB}$$
$$= \left(-\frac{1}{2}\cos\Phi - \frac{\sqrt{3}}{2}\sin\Phi\right) + I_{NRB}$$
$$I\left(\frac{4\pi}{3}\right) = I\left(-\frac{1}{2}\cos\Phi + \frac{\sqrt{3}}{2}\sin\Phi\right) + I_{NRB}$$

Equations (7), given below, are obtained by eliminating $I_{NRB}$ from Equations (6).

$$\left\{I\left(\frac{2\pi}{3}\right) - I\left(\frac{4\pi}{3}\right)\right\}^2 = (\sqrt{3}\,I)^2(\sin\Phi)^2 \quad \text{Equations (7)}$$
$$\left\{I\left(\frac{2\pi}{3}\right) + I\left(\frac{4\pi}{3}\right) - 2I(0)\right\}^2 = (3I)^2(\cos\Phi)^2$$

Equation (8), given below, is obtained by dividing both sides of the first equation of Equations (7) by 3, dividing both sides of the second equation of Equations (7) by 9, and then adding the equations together to eliminate $\Phi$.

$$I = \sqrt{\left\{\frac{I\left(\frac{2\pi}{3}\right) - I\left(\frac{4\pi}{3}\right)}{\sqrt{3}}\right\}^2 + \left\{\frac{I\left(\frac{2\pi}{3}\right) + I\left(\frac{4\pi}{3}\right) - 2I(0)}{3}\right\}^2} \quad \text{Equation (8)}$$

The optical detection processing according to the present exemplary embodiment can also be executed according to the flowchart illustrated in FIG. 6. In such cases, the number of modulation phases N=3 may be set at step S102, and modulation may be performed at the modulation phases 0, 2π/3, 4π/3 at step S108.

Figure 9:
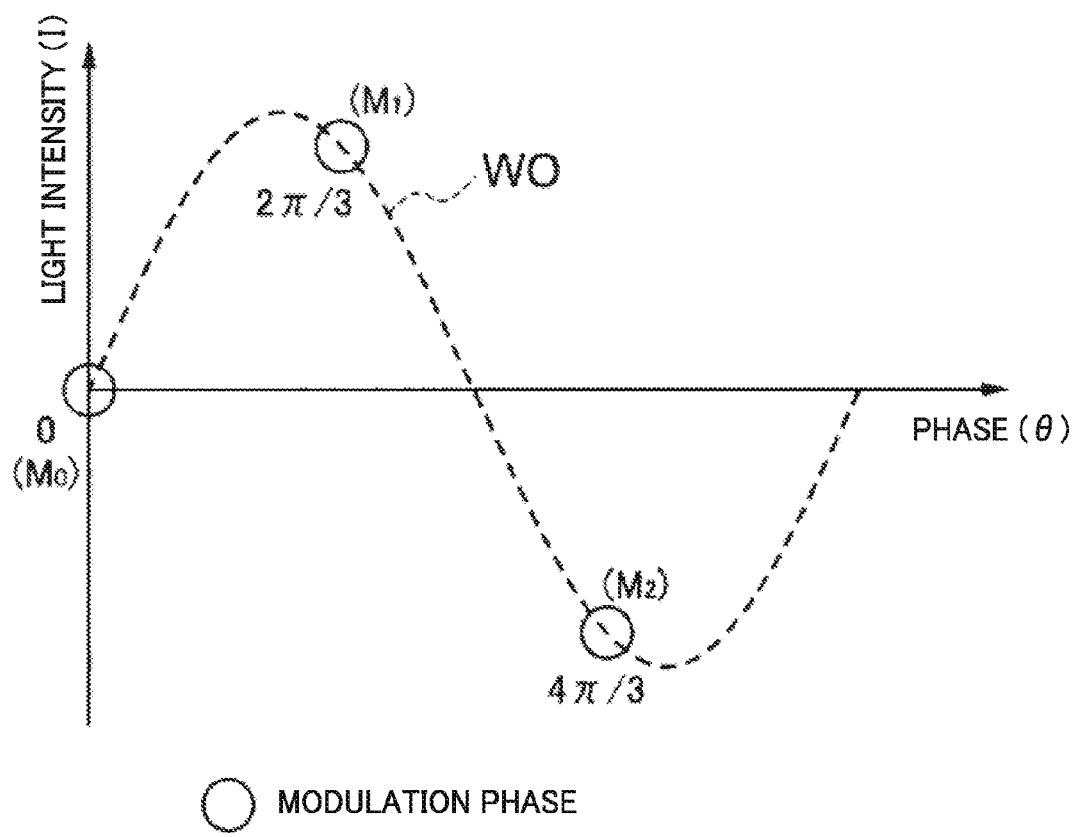
FIG. 9 is a schematic diagram for explaining modulation phases of phase modulation according to a third exemplary embodiment.
Figure 10:
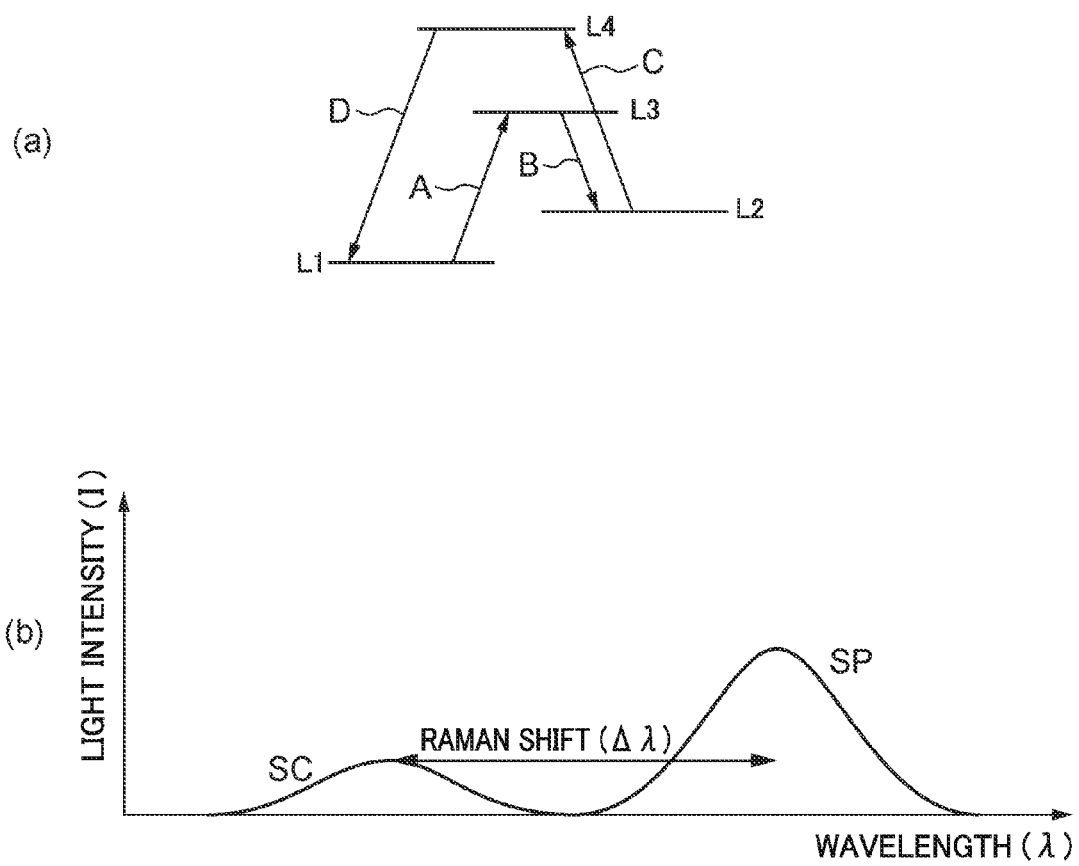
FIG. 10 shows diagrams for explaining Raman scattering.
Figure 11:
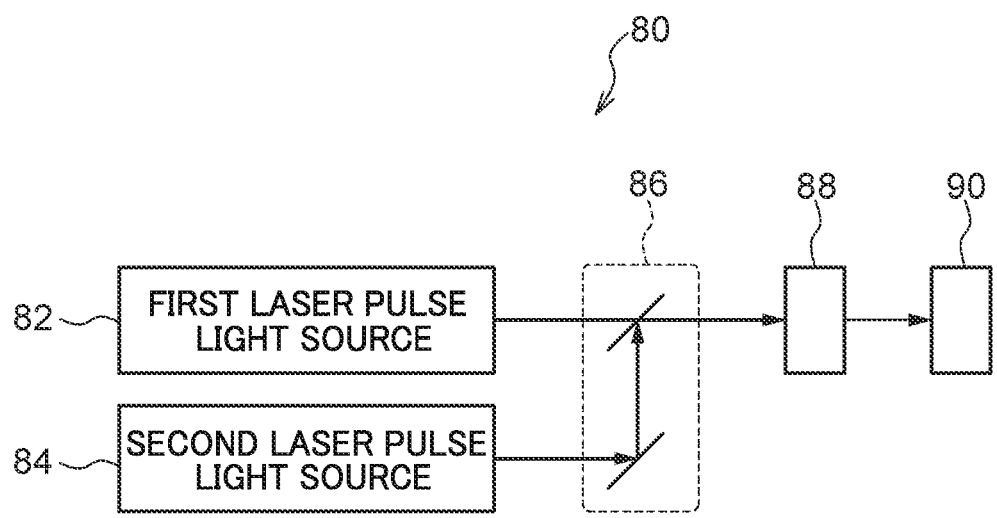
FIG. 11 is a block diagram illustrating a configuration of a Raman spectroscopy device according to related technology.
Figure 12:
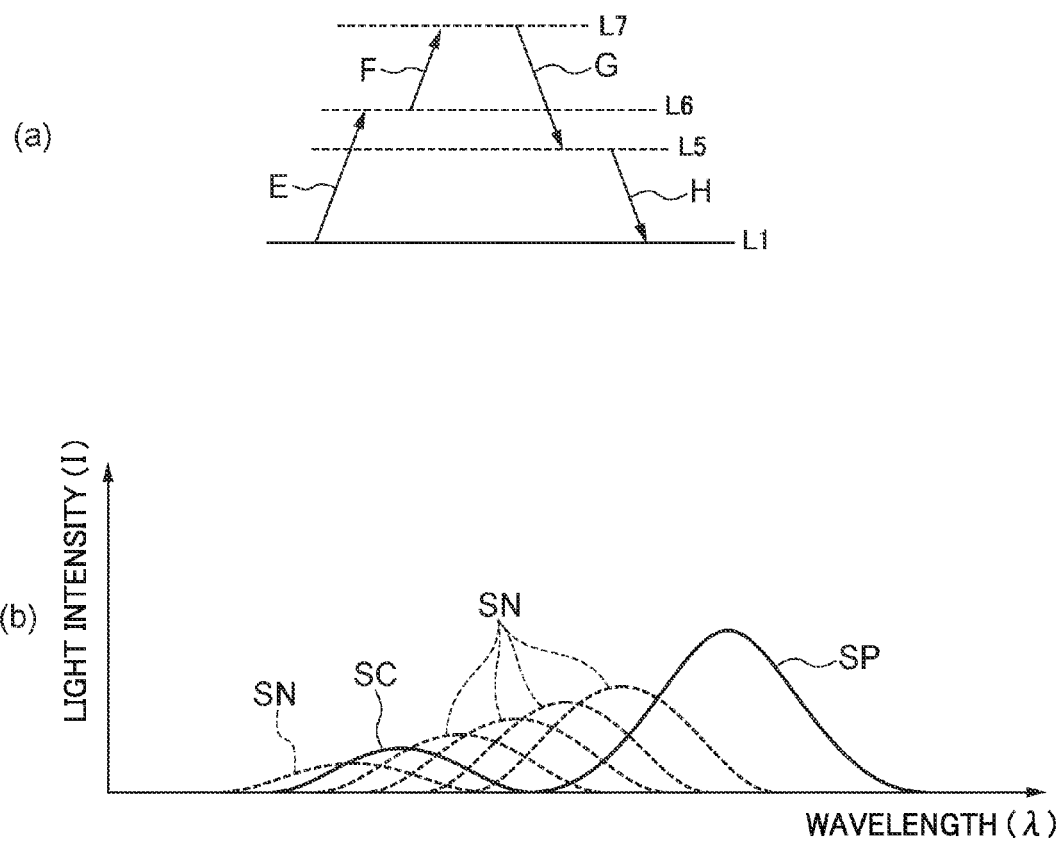
FIG. 12 is a diagram for explaining a non-resonant background.
Figure 13:
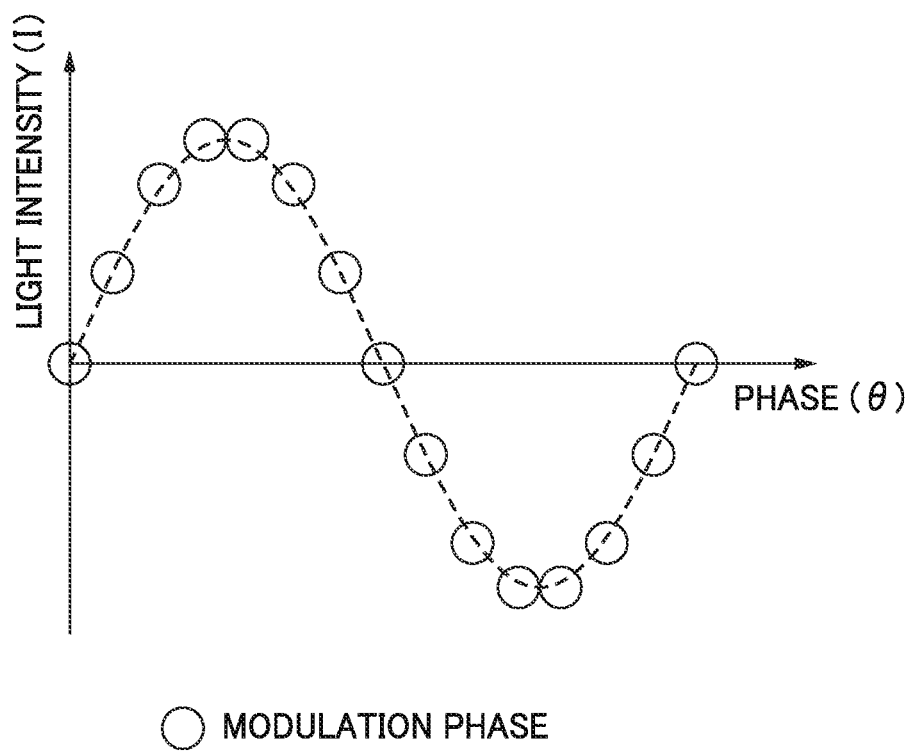
FIG. 13 is a diagram for explaining phase modulation according to related technology.

FIG. 9 illustrates modulation phases when the number of modulation phases N is 3. As illustrated in FIG. 9, in the present exemplary embodiment, phase modulation may be performed over one period of the waveform WO of the light of the pulsed light PB at reference phase position $M_0$ of phase 0, phase position $M_1$ of phase 2π/3, and phase position $M_2$ of phase 4π/3.

Since the number of phase modulations N is 3, the present exemplary embodiment has the merit of enabling the calculation time for the frequency spectrum extraction to be reduced to approximately ¾ of that of the exemplary embodiments described above in which the number of phase modulations N is 4. Moreover, the modulation phases, 0, 2π3, 4π/3, according to the present exemplary embodiment are not orthogonal. Namely, the present invention can be applied even when the modulation phases are not orthogonal to one another. It is also obviously possible to set the number of modulation phases N to 3 and make the modulation phases orthogonal to each other. For example, 0, π/2, and π may be selected as the modulation phases.

As described above, the present invention enables generalized application be made to plural numbers of modulation phases N, and enables application to be made to plural modulation phases that are not orthogonal.

Note that although explanation has been given in each of the exemplary embodiments described above regarding examples of modes in which a CARS light spectrum is observed, there is no limitation thereto, and a mode may be employed in which signal light from the sample 26 is formed into images at each of, for example, specific spectrum widths.

Although explanation has been given in each of the exemplary embodiments described above regarding examples of modes in which frequency spectra are extracted based on analytically derived calculation equations (Equation (1), Equation (8)), there is no limitation thereto, and, for example, a mode may be employed in which the frequency spectrum is extracted based on an approximate equation under the condition that the light intensity $I(\phi_N)$ converges to the vicinity of 0.

Moreover, although explanation has been given in each of the exemplary embodiments described above regarding examples of modes in which a phase 0 is selected as a reference when selecting phases, there is no limitation thereto, and a fixed phase φ may be selected as the reference since it is sufficient to preserve the relative relationship between the N phases. Namely, for example, the respective phases when the number of modulation phases N is 4 may be selected as 0+φ, π/2+φ, π+φ, and 3π/2+φ.

The disclosure of Japanese Patent Application No. 2014-033129 is incorporated in its entirety by reference herein.

All cited documents, patent applications, and technical standards mentioned in the present specification are incorporated by reference in the present specification to the same extent as if each individual cited document, patent application, or technical standard was specifically and individually indicated to be incorporated by reference.

EXPLANATION OF THE REFERENCE NUMERALS 10 optical detection device
12 light source
14 optical modulator
16 spectroscope
18 optical receiver
20 controller
22 signal generator
24 bandpass filter
26 sample
28 shortpass filter
30, 32 objective lens
34A, 34B retroreflector
36A, 36B, 36C reflector
38 drive mechanism-equipped retroreflector
80 Raman spectroscopy device
82 first laser pulse light source
84 second laser pulse light source
86 optical system
88 sample
90 detection device
100 optical detection device
Sm spectrum marker

The invention claimed is:

1. An optical detection device comprising:
a light source section that generates a first pulsed light;
a filter section that transmits a second pulsed light formed from a portion of a frequency spectrum exhibited by the first pulsed light, and that reflects a third pulsed light formed from another portion of the frequency spectrum exhibited by the first pulsed light;
a phase modulation section that phase modulates the second pulsed light at a plurality of phases;
a multiplexing section that produces a fourth pulsed light by multiplexing the third pulsed light with the second pulsed light phase modulated by the phase modulation section;
a detector that spectrally disperses and detects scattered light generated by radiating the fourth pulsed light onto a target object; and
an extraction section that uses calculation processing of (1) or (2) to synchronize with the phase modulation in the phase modulation section, so as to extract a frequency spectrum of scattered light scattered based on the second pulsed light phase modulated by the phase modulation section from the frequency spectrum of the scattered light detected by the detector, wherein (1) and (2) are as follows:
(1) the plurality of phases are φ, φ+2π/3, and φ+4π/3 (where φ is a fixed phase), and the extraction section extracts a frequency spectrum in which the value of I is 0 or a value within an acceptable range of 0, where I is expressed by the equation below for respective intensities I(φ), I(φ+2π/3), and I(φ+4π/3) at the plurality of phases of the scattered light detected by the detector:

$$I = \sqrt{\left\{\frac{I\left(\phi + \frac{2\pi}{3}\right) - I\left(\phi + \frac{4\pi}{3}\right)}{\sqrt{3}}\right\}^2 + \left\{\frac{I\left(\phi + \frac{2\pi}{3}\right) + I\left(\phi + \frac{4\pi}{3}\right) - 2I(\phi)}{3}\right\}^2}$$

(2) the plurality of phases are φ, φ+π/2, φ+π, and φ+3π/2 (where φ is a fixed phase), and the extraction section extracts a frequency spectrum in which the value of I is 0 or a value within an acceptable range of 0, where I is expressed by the equation below for respective intensities I(φ), I(φ+π/2), I(φ+π), and I(φ+3π/2) at the plurality of phases of the scattered light detected by the detector:

$$I = \sqrt{\{I(\phi) - I(\phi + \pi)\}^2 + \left\{I\left(\phi + \frac{\pi}{2}\right) - I\left(\phi + \frac{3\pi}{2}\right)\right\}^2}.$$

2. The optical detection device of claim 1, wherein:
the light source section is a light source that employs an ultrashort pulse laser; and
the bandwidth of the frequency spectrum of the second pulsed light is narrower than the bandwidth of the frequency spectrum of the third pulsed light.

3. The optical detection device of claim 1, wherein the phase modulation section is a modulator based on electro-optical effects, or a light path length adjustment section that changes a light path length for incident light and emits the incident light.

4. The optical detection device of claim 1, wherein the filter section and the multiplexing section are configured by a single bandpass filter that transmits the second pulsed light and the second pulsed light phase modulated by the phase modulation section, and that reflects the third pulsed light.

5. The optical detection device of claim 1, wherein the frequency spectrum extracted by the extraction section is a frequency spectrum of coherent anti-Stokes Raman scattered light.

6. An optical detection method comprising:
in a filter section, transmitting a second pulsed light formed from a portion of a frequency spectrum exhibited by a first pulsed light emitted by a light source section, and reflecting a third pulsed light formed from another portion of the frequency spectrum exhibited by the first pulsed light;
phase modulating the second pulsed light at a plurality of phases using a phase modulation section;
producing a fourth pulsed light by using a multiplexing section to multiplex the third pulsed light and the second pulsed light phase modulated by the phase modulation section;
spectrally dispersing scattered light generated by radiating the fourth pulsed light onto a target object and detecting the spectrally dispersed scattered light with a detector; and
synchronizing with the phase modulation in the phase modulation section by using calculation processing of (1) or (2), so as to extract a frequency spectrum of scattered light scattered based on the second pulsed light phase modulated by the phase modulation section from the frequency spectrum of the scattered light detected by the detector, wherein (1) and (2) are as follows:

(1) the plurality of phases are $\phi$, $\phi+2\pi/3$, and $\phi+4\pi/3$ (where $\phi$ is a fixed phase), and the extraction section extracts a frequency spectrum in which the value of I is 0 or a value within an acceptable range of 0, where I is expressed by the equation below for respective intensities $I(\phi)$, $I(\phi+2\pi/3)$, and $I(\phi+4\pi/3)$ at the plurality of phases of the scattered light detected by the detector:

$$I = \sqrt{\left\{\frac{I\left(\phi+\frac{2\pi}{3}\right) - I\left(\phi+\frac{4\pi}{3}\right)}{\sqrt{3}}\right\}^2 + \left\{\frac{I\left(\phi+\frac{2\pi}{3}\right) + I\left(\phi+\frac{4\pi}{3}\right) - 2I(\phi)}{3}\right\}^2}$$

(2) the plurality of phases are $\phi$, $\phi+\pi/2$, $\phi+\pi$, and $\phi+3\pi/2$ (where $\phi$ is a fixed phase), and the extraction section extracts a frequency spectrum in which the value of I is 0 or a value within an acceptable range of 0, where I is expressed by the equation below for respective intensities $I(\phi)$, $I(\phi+\pi/2)$, $I(\phi+\pi)$, and $I(\phi+3\pi/2)$ at the plurality of phases of the scattered light detected by the detector:

$$I = \sqrt{\{I(\phi) - I(\phi+\pi)\}^2 + \left\{I\left(\phi+\frac{\pi}{2}\right) - I\left(\phi+\frac{3\pi}{2}\right)\right\}^2}.$$

7. A non-transitory computer-readable storage medium storing a program that controls an optical detection device comprising a light source section that generates a first pulsed light, a filter section that transmits a second pulsed light formed from a portion of a frequency spectrum exhibited by the first pulsed light, and that reflects a third pulsed light formed from another portion of the frequency spectrum exhibited by the first pulsed light, a phase modulation section that phase modulates the second pulsed light at a plurality of phases, a multiplexing section that produces a fourth pulsed light by multiplexing the third pulsed light with the second pulsed light phase modulated by the phase modulation section, and a detector that spectrally disperses and detects scattered light generated by radiating the fourth pulsed light onto a target object, the program causing a computer to function as:
an extraction section that uses calculation processing of (1) or (2) to synchronize with the phase modulation in the phase modulation section, so as to extract a frequency spectrum of scattered light scattered based on the second pulsed light phase modulated by the phase modulation section from the frequency spectrum of the scattered light detected by the detector, wherein (1) and (2) are as follows:

(1) the plurality of phases are $\phi$, $\phi+2\pi/3$, and $\phi+4\pi/3$ (where $\phi$ is a fixed phase), and the extraction section extracts a frequency spectrum in which the value of I is 0 or a value within an acceptable range of 0, where I is expressed by the equation below for respective intensities $I(\phi)$, $I(\phi+2\pi/3)$, and $I(\phi+4\pi/3)$ at the plurality of phases of the scattered light detected by the detector:

$$I = \sqrt{\left\{\frac{I\left(\phi+\frac{2\pi}{3}\right) - I\left(\phi+\frac{4\pi}{3}\right)}{\sqrt{3}}\right\}^2 + \left\{\frac{I\left(\phi+\frac{2\pi}{3}\right) + I\left(\phi+\frac{4\pi}{3}\right) - 2I(\phi)}{3}\right\}^2}$$

(2) the plurality of phases are $\phi$, $\phi+\pi/2$, $\phi+\pi$, and $\phi+3\pi/2$ (where $\phi$ is a fixed phase), and the extraction section extracts a frequency spectrum in which the value of I is 0 or a value within an acceptable range of 0, where I is expressed by the equation below for respective intensities $I(\phi)$, $I(\phi+\pi/2)$, $I(\phi+\pi)$, and $I(\phi+3\pi/2)$ at the plurality of phases of the scattered light detected by the detector:

$$I = \sqrt{\{I(\phi) - I(\phi+\pi)\}^2 + \left\{I\left(\phi+\frac{\pi}{2}\right) - I\left(\phi+\frac{3\pi}{2}\right)\right\}^2}.$$

* * * * *